(12) United States Patent
Biedermann et al.

(10) Patent No.: US 7,722,649 B2
(45) Date of Patent: May 25, 2010

(54) DYNAMIC STABILIZATION DEVICE FOR BONES, IN PARTICULAR FOR VERTEBRAE

(75) Inventors: Lutz Biedermann, VS-Villingen (DE); Dezsö Jeszensky, St. Gallen (CH)

(73) Assignee: Biedermann Motech GmbH, VS-Schwenningen (DE)

( * ) Notice: Subject to any disclaimer, the term of this patent is extended or adjusted under 35 U.S.C. 154(b) by 368 days.

(21) Appl. No.: 10/637,349

(22) Filed: Aug. 7, 2003

(65) Prior Publication Data
US 2004/0049190 A1  Mar. 11, 2004

(30) Foreign Application Priority Data
Aug. 9, 2002  (DE)  ............... 102 36 691

(51) Int. Cl.
*A61B 17/70*  (2006.01)
(52) U.S. Cl. ............... 606/257; 606/266; 606/276
(58) Field of Classification Search ............... 606/61, 606/74, 72, 60, 70, 71, 76, 77, 90, 105, 80 A, 606/264, 266, 254, 272, 908, 257, 276
See application file for complete search history.

(56) References Cited

U.S. PATENT DOCUMENTS

| | | | |
|---|---|---|---|
| 5,423,816 A |  | 6/1995 | Lin |
| 5,540,688 A | * | 7/1996 | Navas ............... 606/61 |
| 5,554,157 A | * | 9/1996 | Errico et al. ............... 606/61 |
| 5,562,660 A | * | 10/1996 | Grob ............... 606/258 |
| 5,672,175 A | * | 9/1997 | Martin ............... 606/61 |
| 5,733,284 A | * | 3/1998 | Martin ............... 606/61 |
| 5,961,517 A | * | 10/1999 | Biedermann et al. ............... 606/61 |
| 6,162,223 A |  | 12/2000 | Orsak et al. ............... 606/59 |
| 6,267,764 B1 |  | 7/2001 | Elberg |
| 6,440,169 B1 |  | 8/2002 | Elberg et al. |
| 2003/0220643 A1 | * | 11/2003 | Ferree ............... 606/61 |

FOREIGN PATENT DOCUMENTS

| | | |
|---|---|---|
| DE | 2821678 | 11/1979 |
| DE | 42 39 716 C1 | 8/1994 |

(Continued)

*Primary Examiner*—Pedro Philogene
(74) *Attorney, Agent, or Firm*—Christie, Parker & Hale LLP

(57) ABSTRACT

A dynamic stabilization device for bones, in particular vertebrae, is made with two bone anchoring elements and a rigid rod with a longitudinal axis connecting them. An elastic element is inserted between the two bone anchoring elements. It acts on the bone anchoring elements to exert a force in a direction of the longitudinal axis. Each bone anchoring element has a first section to be anchored in a bone and a second section to be connected to the rod. At least one of the bone anchoring elements is fixedly connected to the rod to prevent translational movement of the rod relative to it. Further, at least one of the bone anchoring elements is a polyaxial bone screw. Also disclosed is a method for stabilizing vertebrae adjacent to a defective intervertebral disc. A dynamic stabilization device is provided. The anchoring elements are attached to two vertebrae on opposite sides of the defective intervertebral disc. Then, the bone anchoring elements are alligned to connect the rod therebetween with the elastic element positioned between the bone anchoring elements. Finally, one of the bone anchoring elements is connected fixedly to the rod to prevent translational movement of the rod relative to it.

22 Claims, 2 Drawing Sheets

FOREIGN PATENT DOCUMENTS

| | | | |
|---|---|---|---|
| EP | 0 677 277 A2 | 10/1995 | |
| EP | 0 516 567 B1 | 7/1997 | |
| EP | 0 669 109 B1 | 5/1999 | |
| FR | 2 717 370 | 9/1995 | |
| FR | 2717370 * | 9/1995 | ................ 606/61 |
| FR | 2 805 451 A1 | 2/2000 | |
| SU | 848009 | 7/1981 | |
| WO | WO96/32071 | 10/1996 | |
| WO | WO 00/15125 | 3/2000 | |
| WO | WO 01/08574 * | 2/2001 | ................ 606/61 |
| WO | WO 01/08574 A1 | 2/2001 | |

\* cited by examiner

DYNAMIC STABILIZATION DEVICE FOR BONES, IN PARTICULAR FOR VERTEBRAE

FIELD OF THE INVENTION

The invention relates to a dynamic stabilization device for bones, in particular for vertebrae, preferably with at least one first and one second bone anchoring element, and a rod connecting the bone anchoring elements, wherein each bone anchoring element has a first section to be anchored in a bone and a second section to be connected to a rod, and wherein the bone anchoring elements can optionally be connected to the rod rigidly or as displaceable in the direction of the shaft of the rod.

BACKGROUND OF THE INVENTION

A known method for treating intervertebral disc defects is removal by operation of the defective intervertebral disc and stiffening the intervertebral disc space with two vertebral bodies or, after removal of the defective intervertebral disc, subsequent insertion of an artificial intervertebral disc. In the first case, the sections of the vertebral column adjacent to the stiffened section are unnaturally stressed and, in the second case, simulation of the properties of a natural intervertebral disc is still unsatisfactory.

EP 0 669 109 B1 describes a device for stabilizing adjacent thoracic vertebrae, with which a damaged intervertebral disc and the intervertebral joints can be partly relieved from stress posteriorly. The device has two pedicle screws, which are rigidly connected in each case to a band consisting of an elastic synthetic material and are connected to one another via the biased band. To transmit pressure forces, a compression-proof body pushed on to the elastic band is further provided between the two screw heads. The use of a band of this kind does not however produce any guidance stability of the movement segment of a vertebral column. Nor is it possible to adjust the adjacent vertebrae in their positioning relative to one another, because the force transmission behaviour of the band and the pressure element via the bone screws is non-specific.

EP 0 518 567 B1 describes a device for stabilizing adjacent vertebrae, which has a damping element consisting of an elastomer, which is provided between two monoaxial screws screwed into the vertebrae. Each end of the damping element is connected a spherical head of the bone screw, which can be inserted into a receiving part of the bone screw and fixed therein. Thus, a minimal adjustment of the angle of the bone screw relative to the longitudinal axis of the damping element is possible. However, for each pair of vertebrae to be connected to one another an individually matching damping element with exact length and exact cross-section has to be made. Furthermore, the force transmission behaviour of the damping element is undefined, as it yields not only to axial, but also to bending and torsional forces.

It is further known to provide for fixing the vertebral column or sections of the vertebral column with an implant system consisting of a rod and at least two pedicle screws rigidly connected to the rod and screwed into corresponding vertebrae. However, with this implant system it is not possible to provide for dynamic movement control of the intervertebral disc or for dynamic takeover of stress to relieve the stress on a intervertebral disc.

U.S. Pat. No. 5,672,175 describes a dynamic implanted spinal orthosis which attempts to preserve at least in part the natural mobility of the vertebrae while effecting and maintaining a correction of the relative positions of the vertebrae without osteosynthesis, graft or fusion. As such, anchoring components are fixed to the vertebrae, each anchoring component comprising at least one plate having an anterior convex face coming to bear in contact with the vertebral lamina on at least one side of the spinous process. Cylinders of the coupling means are carried by a plate opposite the transverse end of the lamina near the transverse process. Each plate is fixed to a vertebrae on at least two different places, for example, by an intrapedicular screw and/or clamping hooks. Holding means are coupled to the plates, the holding means comprising an elastic return device for exerting forces for holding the vertebrae in the corrected position against natural deforming forces, thus treating a deformation of the spine.

U.S. Pat. No. 5,733,284 describes a device for anchoring rachidian instrumentation on a vertebrae. The device has structure very similar to the device described in U.S. Pat. No. 5,672,175.

It is still desirable to provide new and better dynamically acting stabilization devices for bones, in particular for adjacent vertebrae, with which it is possible both to position the bones or vertebrae and intervertebral joints in respect of one another and simultaneously, in a defined way, to support and partially relieve the stress on the intervertebral disc and intervertebral joints connected in between with respect to the forces to be transmitted.

SUMMARY OF THE INVENTION

The present invention provides a dynamic stabilization device for bones, in particular for vertebrae. In accord with the present invention, a dynamic stabilization device comprises two bone anchoring elements and a rod connecting them. Each bone anchoring element has a first section to be anchored in a bone and a second section to be connected to the rod. Optionally, each bone anchoring element can be connected to the rod rigidly or in such manner that it is displaceable in the direction of the longitudinal axis of the rod. An element is arranged between the bone anchoring elements, which can be elastically biased in the direction of the longitudinal axis of the rod.

In one embodiment of the invention, one of the bone anchoring elements preferably is connected displaceably to the rod and a stop, which is provided to limit the movement of the displaceable bone anchoring element.

In another embodiment, at least one bone anchoring element preferably is connected polyaxially to the rod.

In a further embodiment of the invention, the bone anchoring element has a shank for anchoring in the bone and a receiving part that is connected in an articulated manner to the shank for receiving the rod. Preferably, the shank and the receiving part are fixed relative to one another in an angle independently of fixing of the rod. In addition, the polyaxial bone anchoring element preferably is arranged displaceably connected to the rod and adjacent to the stop.

In certain preferred embodiments of the invention, at least one of the bone anchoring elements is rigidly connected to the rod.

In still another embodiment of the invention, the rod and/or parts of one of the bone anchoring elements is/are coated with a sliding material (a material having a low coefficient of friction).

In embodiments of the invention having an elastically biased element arranged between the bone anchoring elements, preferably the elastically biased element comprises a spring. More preferably, the elastically biased element comprises a helical spring, which surrounds the rod.

In further embodiments of the invention, the rod comprises two pieces comprising a sleeve and the spring is provided inside the rod.

Typically, the bone anchoring elements are constructed as bone screws or bone hooks.

The invention also provides a method for stabilizing vertebrae adjacent to a defective intervertebral disc. The method comprises the following steps: providing a dynamic stabilization device comprising a first bone anchoring element, a second bone anchoring element, a rigid rod having a longitudinal axis connecting the two bone anchoring elements and an elastic element between the first and the second bone anchoring element and acting on the first and the second bone anchoring element to exert a force in a direction of the longitudinal axis, wherein each bone anchoring element comprises a first section to be anchored in a bone and a second section to be connected to the rod, and wherein at least one of the bone anchoring elements comprising a polyaxial bone screw; attaching the first and second bone anchoring elements to two vertebrae on opposite sides of the defective intervertebral disc; aligning the second section of both of the first and second bone anchoring elements to connect the rod therebetween with the elastic element positioned between the first and second bone anchoring elements; and fixedly connecting at least one of the bone anchoring elements to the rod so as to prevent translational movement of the rod relative to the at least one of the bone anchoring elements.

Further features and advantages of the invention will become apparent from the detailed description and the drawings.

DETAILED DESCRIPTION OF THE INVENTION INCLUDING PREFERRED EMBODIMENTS

The invention is now described in detail with reference to the embodiment illustrated in FIGS. 1 to 4. A stabilization device in accord with one embodiment of the present invention has two polyaxial pedicle screws 1, 2 and a rod 3 connecting them for stabilizing two adjacent vertebrae 100, 101. The stabilization device further contains a spring element 30, provided between the two pedicle screws.

Figure 3:
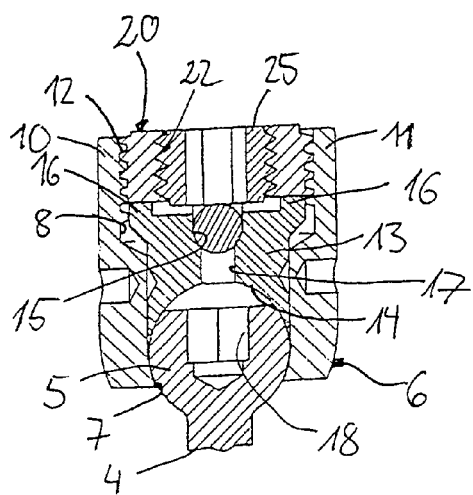
FIG. 3 shows a sectional illustration of a polyaxial screw used in the device taken along line A—A in FIG. 1.
Figure 4:
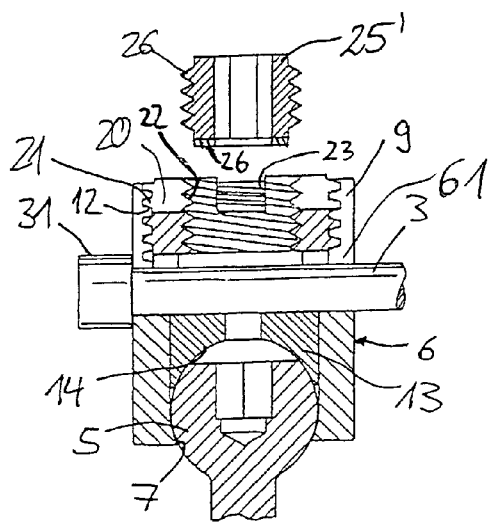
FIG. 4 shows an illustration in partial section of a polyaxial screw illustrated in FIG. 1 taken along the line B—B in FIG. 2.

The pedicle screws 1, 2 preferably are constructed as illustrated in FIGS. 3 and 4. A pedicle screw 1, 2 has a screw element with a threaded shank 4 with a bone thread and a head 5 shaped like a segment of a sphere, which is connected to a receiving part 6. The receiving part 6 has on one of its ends a first bore 7, aligned symmetrically to the axis, the diameter of which is larger than that of the threaded section of the shank 4 and smaller than that of the head 5. It further has a coaxial second bore 8 which is open at the end opposite the first bore 7 and the diameter of which is large enough for the screw element to be guided through the open end with its threaded section through the first bore 7 and with its head 5 as far as the floor of the second bore. The floor of the receiving part is constructed in such a way that the screw element in the inserted and unstressed state is swivellable in the receiving part 6. The receiving part further has a U-shaped recess 61 shown in FIG. 4 which is arranged symmetrical towards the center and the floor of which is directed towards the first bore 7 and by which two open legs 10, 11 are formed. In an area bordering on the open end the legs 10, 11 have an inner thread 12.

The pedicle screw additionally contains a pressure element 13, which is constructed with a suitable outer diameter in such a way that it can be pushed into the receiving part 6. On one of its ends a recess 14 is provided, shaped like a segment of a sphere and widening towards the first bore 7 of the receiving part 6, and the spherical radius of which is chosen in such a way that in a state inserted into the receiving part it surrounds the head 5 of the screw element. In the direction of the open end of the legs 10, 11 the pressure element 13 has a U-shaped recess 15, the dimensions of which are so dimensioned that the rod 3 can be placed into the thereby formed channel. The depth of the U-shaped recess 15, seen in the direction of the cylindrical axis of the receiving part 6, is greater than the diameter of the rod 3 to be received, so the pressure element 13 projects upwards with lateral legs 16 above the placed in rod 3. The pressure element 13 further has a central bore 17 which extends through it to permit a screw tool to engage a corresponding recess 18 provided in the head 5.

For fixing the screw element in the receiving part a bushing-type or nut-type locking element 20 is provided which can be screwed in between the legs 10, 11 and which has an outer thread 21 which cooperates with the inner thread 12 of the legs and further has an inner thread 22. For screwing in, the locking element 20 further has radially running indents 23 on one of its ends. The dimensions of the locking element 20 in the axial direction of the receiving part and the dimensions of the open legs 10, 11 of the receiving part and the dimensions of the cooperating threads or the height of the open legs 16 of the pressure element are dimensioned in such a way that in the screwed in state the locking element 20 exerts a force on the legs 16 of the pressure element, so it blocks the head 5 in the receiving part 6. Thus, the angle of the cylindrical axis of the receiving part relative to the longitudinal axis of the screw element can be fixed variably.

Furthermore, an inner screw or clamping or setting screw 25, which can be screwed into the locking element 20 is provided, the outer thread 26 of which cooperates with the inner thread 22 of the locking element 20. The dimensions of the inner screw 25, the locking element 20 and the pressure element 13 are chosen in such a way that in the screwed in state the inner screw 25 presses on the placed in rod 3.

Figure 1:
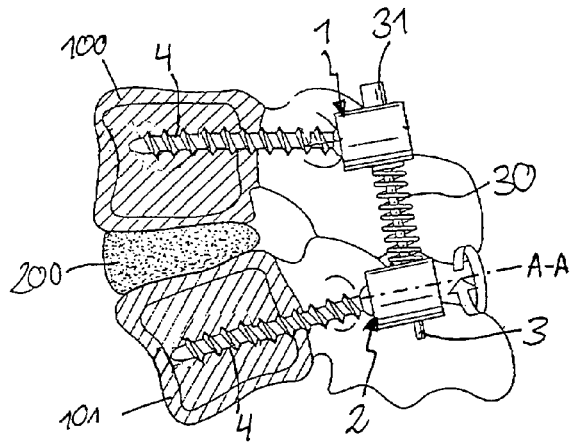
FIG. 1 shows a schematic side view of the device according to the invention in an assembled state in vertebrae.
Figure 2:
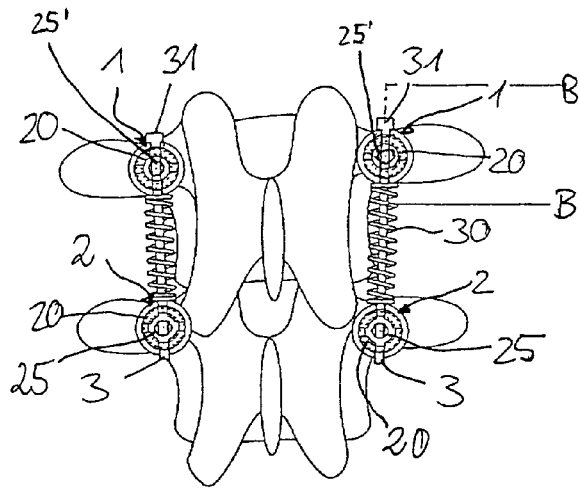
FIG. 2 shows a horizontal projection on to the device as illustrated in FIG. 1.

FIG. 4 shows a section through the pedicle screw 1 according to FIGS. 1 and 2. Pedicle screw 1 differs from pedicle screw 2 in the construction of the inner screw. As can be seen from FIG. 4, the inner screw 25' of the pedicle screw 1 has on its side facing the rod a sliding floor 26 made of a sliding material in order to enable low-friction sliding of the rod in operation. A high molecular weight polyethylene of the UHMWPE type with a molecular weight between $2 \times 10^6$ to $10 \times 10^6$ is used, for example, as sliding material. Other biocompatible materials having low coefficient of friction can also be used. Such materials are well known to those skilled in the art.

The spring element 30 preferably is constructed as a helical spring with a diameter which is slightly larger than the diameter of the rod 3, SO the helical spring can be pushed on to the rod 3. The length of the helical spring in the axial direction is matched to the size of the distance between the adjacent vertebrae to be bridged by the rod between the two pedicle screws. Furthermore, the length of the helical spring and the spring force can be selected by the surgeon and are dimensioned in such a way that an extension or compression effect can be achieved with the spring for an existing functional deficit of the intervertebral disc. The spring is preferably coated with an abrasion-proof material, e.g. with an abrasion-proof synthetic material.

The rod 3 preferably has a stop 31 on one of its ends, e.g. in the form of a ring-shaped shoulder, which has a diameter which is larger than the diameter of the U-shaped recess of the receiving part 6 and the pressure element 13 so that, in the assembled state, the pedicle screw 1 adjacent to the stop 31 is displaceable along the rod only as far as the stop.

Preferably, the rod is coated with a material, in particular, with a suitable material having a low coefficient of friction, which facilitates sliding of the rod in the receiving part 6 or in the pressure element 13 provided for this. Preferably, the pressure element 15 of at least one of the pedicle screws also is coated with a material having a low coefficient of friction which increases the ability to slide, e.g. a synthetic material. Suitable materials include, for example. UHM WPE or anodized metal, such as anodized titanium.

Figure 5:
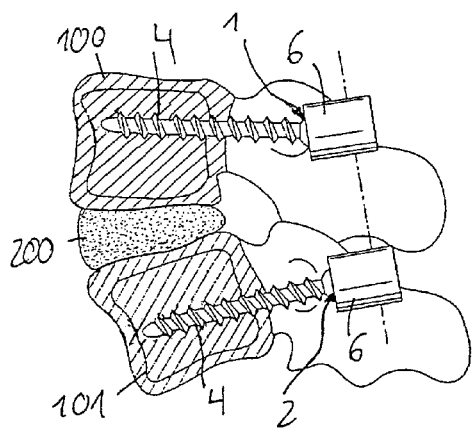
FIG. 5 to FIG. 8 illustrate a sequence of steps showing the assembly of the stabilization device in vertebrae.
Figure 6:
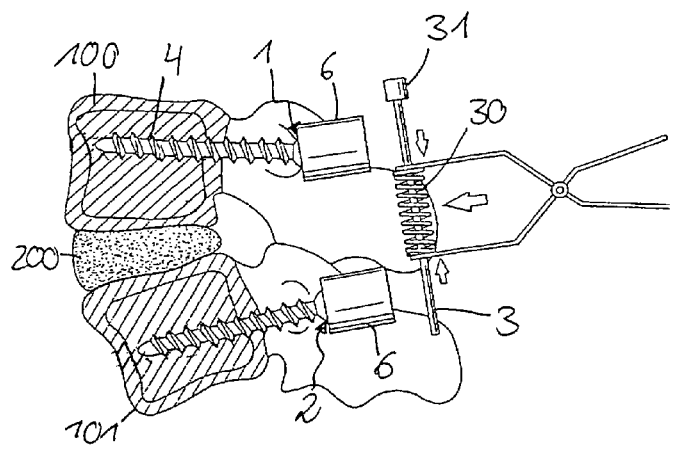

In operation, as can be seen from FIG. 5, first the screw elements of the pedicle screws 1, 2, which have been inserted into the receiving parts 6, are screwed by the surgeon into the vertebrae of a patient adjacent to a defective intervertebral disc 200 in the unstressed state and the receiving parts 6 are aligned in such a way that the rod 3 can be inserted into the U-shaped recesses in the receiving parts 6. The pressure elements 13 can be pre-assembled into the receiving parts and access to the screw head through bore 17 to insert the screws into the vertebrae. Alternatively, the pressure elements can be inserted after the screws have been inserted into the vertebrae. Next, as shown in FIG. 6, the rod 3 is inserted into the receiving parts 6 with the spring 30 assembled on to it. The rod 3 preferably is oriented therein in such a way that the stop 31 points in the direction of the patient's head. Further, the spring 30 is pre-compressed by means of a tool, in order to bring it between the two receiving parts 6 at a bias.

Figure 7:
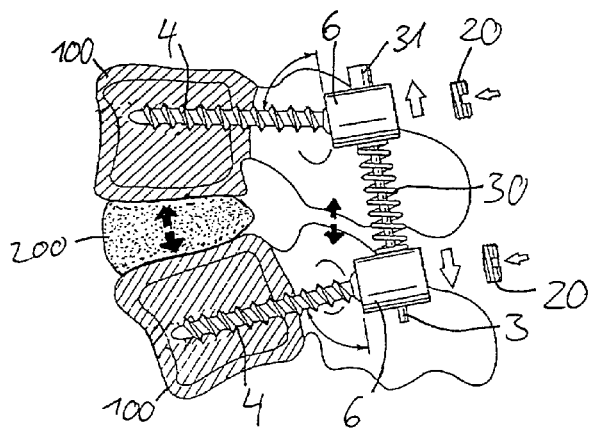

In the next step, illustrated in FIG. 7, the surgeon sets the optimum angle of screw element to receiving part or rod for each of the pedicle screws 1, 2. This angle is then fixed by screwing the locking elements 20 into the receiving parts. As can be seen from FIGS. 3 and 4, fixing of the angle takes place in that the locking element 20 exerts a force on the pressure element 13 in such a way that it fixes the head 5 in its position in the receiving part such that the angle between the longitudinal axis of the screw and the cylindrical axis of the receiving head is fixed as desired by the surgeon. Because the legs 16 of the pressure element project beyond the placed in rod 3, the rod 3 is not touched by screwing in the locking element 20 and is still freely displaceable in the receiving part 6 in each case.

By means of the angle of the screw element and the receiving part to one another a desired wedge angle can be set between the opposite surfaces of the adjacent vertebrae, which enables the intervertebral disc located in between to adopt its natural shape again. By using two stabilization devices in each case, as shown in FIG. 2, the setting of the angle is therein possible in lateral and front view independently of one another. In this way the position of the intervertebral joints to one another also can be defined.

As can be seen further from FIG. 7, the spring 30 inserted under bias expands after insertion and, thus, presses apart the two receiving parts 6 connected by the rod. The expansion is limited on one side by the stop 31. The expansion pressure of the spring causes a widening out of the intervertebral space and the intervertebral joints to take place, whereby the intervertebral disc 200 can expand owing to absorbing fluid from the intervertebral space and the intervertebral joints are freed from stress, as depicted by the arrows in FIG. 7. A damaged intervertebral disc can thus adopt its natural shape again.

Figure 8:
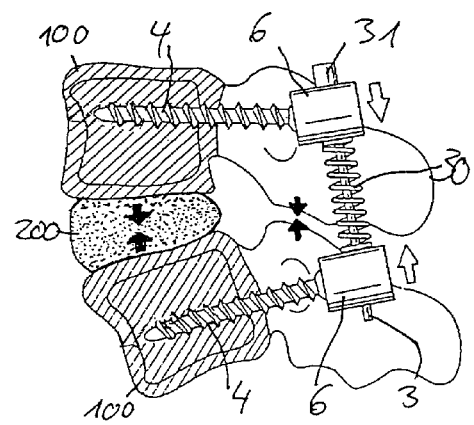

As shown in FIG. 8, the spring then is compressed slightly by moving the receiving parts 6 towards one another in order to bring it under bias again. Thereby, the intervertebral space is also reduced and the intervertebral disc is pressed together or shortened slightly again and the intervertebral joints are stressed, as illustrated by the arrows in FIG. 8. In the desired final position, the rod 3 is rigidly connected to the receiving part 6 of the pedicle screw positioned at the end of the rod 3 opposite the stop 31. Fixing the rod takes place by screwing in the inner screw 25 in the receiving part of the lower pedicle screw 2. However, in the pedicle screw 1 provided adjacent to the stop 31 of the rod the receiving part 6 and the rod 3 remain movable (i.e., longitudinally displaceable) with respect to one another. The inner screw 25' with the sliding floor 26 enables low-friction sliding of the rod.

In the position shown in FIGS. 1 and 2, the dynamic stabilization system in accord with the invention acts as a force transmission and damping system. The forces acting on the vertebral column when the patient is in an upright position are partially transmitted via the system consisting of pedicle screws, spring and rod, so that the stress on the intervertebral disc is lowered. The spring further acts both as an extension element for widening out the intervertebral space in the resting or unstressed state, i.e., while lying down, and as a damper for damping jolts during stresses, such as when walking, for example.

The system has the advantage that optimum adjustment of the bone screws and the rod is possible during assembly. Owing to the rigid connection via the rod, it is possible to transmit axial forces and thus relieve the stress on the intervertebral disc. The system is, however, rigid to bending and torsion, comprising a further advantage in respect of precise force transmission on to the intervertebral disc.

The invention is not limited to the connection of only two polyaxial pedicle screws by a rod. If required, several vertebrae can also be connected to one another, wherein a corresponding number of polyaxial bone screws are placed in each vertebrae being connected. Depending on the desired mobility, a stop is provided at a suitable point on the rod and a corresponding adjacent bone screw held in a manner displaceable relative to the rod.

Although polyaxial bone screws are used in the embodiment example described, the invention is not limited to these. If the anatomy of the corresponding section on the vertebral column allows monoaxial bone screws to be used, the invention also can be used to connect one monoaxial bone screw rigidly to the rod and one monaxial bone screw slideably to the rod. Combinations of monaxial bone screws and polyaxial bone screws also can be used.

The invention has been described in detail with reference to the preferred embodiments. However, those skilled in the art, upon consideration of the disclosure and drawings, may make modifications and improvements within the intended scope of the invention as defined by the claims. For example, the spring element 30 can also be constructed differently. The spring element 30 can be constructed as a helical spring, provided inside the rod. For this purpose the rod is formed in two parts from two sleeves inserted into one another, each of which has a sleeve floor against which the ends of the helical spring rest.

What is claimed is:

1. A dynamic stabilization device for bones, said device comprising:

a first bone anchoring element;
a second bone anchoring element;
a rod having a longitudinal axis connecting the two bone anchoring elements; and
an elastic element between the first and the second bone anchoring elements and acting on the first and the second bone anchoring elements to exert a force in a direction of the longitudinal axis;
each bone anchoring element comprising a first section to be anchored in a bone and a second section to be connected to the rod;
at least one of the bone anchoring elements comprising a polyaxial bone screw wherein the first section of the polyaxial bone screw comprises a shank for anchoring in the bone and the second section of the polyaxial bone screw comprises a receiving part, the receiving part being connected in an articulated manner to the shank for receiving the rod, and wherein the shank and the receiving part can be fixed relative to one another at an angle.

2. The dynamic stabilization device according to claim 1, wherein the rod is a rigid rod.

3. The dynamic stabilization device according to claim 1, wherein at least one of the bone anchoring elements is fixedly connected to the rod so as to prevent translational movement of the rod relative to the at least one of the bone anchoring elements.

4. The dynamic stabilization device according to claim 1, wherein one of the bone anchoring elements is slideably connected to the rod and wherein the device further comprises a stop to limit the movement of the slideably connected bone anchoring element.

5. The dynamic stabilization device according to claim 1, wherein the receiving part has a U-shaped recess forming two legs and the rod is located in the U-shaped recess between the two legs.

6. The dynamic stabilization device according to claim 1, further comprising a stop, wherein the polyaxial bone anchoring element is slideably connected to the rod and and located adjacent to the stop to limit the movement thereof.

7. The dynamic stabilization device according to claim 1, wherein the rod is coated with a material having a low coefficient of friction.

8. The dynamic stabilization device according to claim 7, wherein the material is a high molecular weight polyethylene.

9. The dynamic stabilization device according to claim 1, wherein one of the bone anchoring elements comprises a material having a low coefficient of friction for contacting the rod.

10. The dynamic stabilization device according to claim 9, wherein the material is a high molecular weight polyethylene.

11. The dynamic stabilization device according to claim 1, wherein the elastic element comprises a spring.

12. The dynamic stabilization device according to claim 1, wherein the elastic element comprises a helical spring that is located around the rod.

13. The dynamic stabilization device according to claim 1, wherein the rod comprises two sleeve-shaped sections and the elastic element comprises a spring positioned inside the two sleeve-shaped sections.

14. The dynamic stabilization device according to claim 1, wherein each of the bone anchoring elements comprise a bone screw or a bone hook.

15. The dynamic stabilization device according to claim 1, wherein the rod and the elastic element comprise two pieces.

16. A method for stabilizing vertebrae adjacent to a defective intervertebral disc, the method comprising:
providing a dynamic stabilization device comprising a first bone anchoring element, a second bone anchoring element, a rod having a longitudinal axis connecting the two bone anchoring elements and an elastic element between the first and the second bone anchoring elements and acting on the first and the second bone anchoring elements to exert a force in a direction of the longitudinal axis, wherein each bone anchoring element comprises a first section to be anchored in a bone and a second section to be connected to the rod, and wherein at least one of the bone anchoring elements comprising a polyaxial bone screw, wherein the first section of the polyaxial bone screw comprises a shank for anchoring in the bone and the second section of the polyaxial bone screw comprises a receiving part, the receiving part being connected in an articulated manner to the shank for receiving the rod, and wherein the shank and the receiving part can be fixed relative to one another at an angle;
attaching the first and second bone anchoring elements to two vertebrae on opposite sides of the defective intervertebral disc; and
aligning the second section of both of the first and second bone anchoring elements to connect the rod therebetween with the elastic element positioned between the first and second bone anchoring elements.

17. The method for stabilizing vertebrae according to claim 16, wherein the device further comprises a stop on one end of the rod, the method further comprising:
positioning the device with rod oriented with the stop pointed toward the head of a patient; and
slideably connecting one the bone anchoring elements to the rod adjacent to the stop to limit the movement of the slideably connected bone anchoring element.

18. The method for stabilizing vertebrae according to claim 16, wherein the device further comprises a stop on one end of the rod, the method further comprising:
positioning the device with rod oriented with the stop pointed toward the head of a patient; and
slideably connecting the polyaxial bone screw to the rod adjacent to the stop to limit the movement of the slideably connected bone anchoring element.

19. The method for stabilizing vertebrae according to claim 16, wherein the device comprises a rigid rod.

20. The method for stabilizing vertebrae according to claim 16, further comprising fixedly connecting at least one of the bone anchoring elements to the rod so as to prevent translational movement of the rod relative to the at least one of the bone anchoring elements.

21. A dynamic stabilization device for bones, said device comprising:
a first bone anchoring element;
a second bone anchoring element;
a rod having a longitudinal axis connecting the two bone anchoring elements; and
an elastic element between the first and the second bone anchoring elements and acting on the first and the second bone anchoring elements to exert a force in a direction of the longitudinal axis;
each bone anchoring element comprising a first section to be anchored in a bone and a second section to be connected to the rod;
wherein the first section of each of the first and second bone anchoring elements comprises a shank with a shank axis and the second section of each of the first and second bone anchoring elements comprises a receiving part holding the rod, at least one of the bone anchoring elements comprising a polyaxial bone screw with the receiving part being connected in an articulated manner to the shank for receiving the rod, and wherein the shank and the receiving part can be fixed relative to one another at an angle;

wherein the shanks of the first and second bone anchoring elements are directly attached to their respective receiving parts such that the shank axes intersect the rod.

22. A dynamic stabilization device for bones, said device comprising:
   a first bone anchoring element;
   a second bone anchoring element;
   a rod having a longitudinal axis connecting the two bone anchoring elements; and
   an elastic element between the first and the second bone anchoring elements and acting on the first and the second bone anchoring elements to exert a force in a direction of the longitudinal axis;
   each bone anchoring element comprising a first section to be anchored in a bone and a second section to be connected to the rod;
   at least one of the bone anchoring elements comprising a polyaxial bone screw wherein the first section of the polyaxial bone screw comprises a shank for anchoring in the bone and the second section of the polyaxial bone screw comprises a receiving part, the receiving part being connected in an articulated manner to the shank for receiving the rod, and wherein the shank and the receiving part can be fixed relative to one another at an angle;
   wherein the rod extends into and completely through the receiving part of at least one of the bone anchoring elements.

* * * * *